US 6,582,381 B1

United States Patent
Yehezkeli et al.

(10) Patent No.: US 6,582,381 B1
(45) Date of Patent: Jun. 24, 2003

(54) MECHANICAL POSITIONER FOR MRI GUIDED ULTRASOUND THERAPY SYSTEM

(75) Inventors: Oded Yehezkeli, Kiryath Tivon (IL); David Freundlich, Haifa (IL); Nitzan Magen, Kiryath Tivon (IL); Carlos Marantz, Karmiel (IL); Yoav Medan, Haifa (IL); Skuki Vitek, Haifa (IL); Avi Weinreb, Haifa (IL)

(73) Assignee: TxSonics Ltd., Tirat Carmel (IL)

( * ) Notice: Subject to any disclaimer, the term of this patent is extended or adjusted under 35 U.S.C. 154(b) by 372 days.

(21) Appl. No.: 09/628,964

(22) Filed: Jul. 31, 2000

(51) Int. Cl.[7] .............................................. A61B 5/055
(52) U.S. Cl. .......................... 601/2; 600/410; 600/424; 128/916
(58) Field of Search .................... 601/2–4; 600/437, 600/410, 411, 415, 424; 128/916, 897

(56) References Cited

U.S. PATENT DOCUMENTS

| 5,018,508 A | | 5/1991 | Fry et al. | |
|---|---|---|---|---|
| 5,131,392 A | * | 7/1992 | Jolesz et al. | 600/410 |
| 5,247,935 A | | 9/1993 | Cline et al. | 128/653.2 |
| 5,275,165 A | | 1/1994 | Ettinger et al. | 128/653.2 |
| 5,443,068 A | | 8/1995 | Cline et al. | 128/653.5 |
| 5,531,742 A | * | 7/1996 | Barken | 606/21 |
| 5,590,653 A | * | 1/1997 | Aida et al. | 600/411 |
| 5,624,382 A | * | 4/1997 | Oppelt et al. | 601/2 |
| 5,752,962 A | * | 5/1998 | D'Urso | 128/857 |
| 5,897,495 A | * | 4/1999 | Aida et al. | 600/411 |
| 6,094,760 A | * | 8/2000 | Nonaka et al. | 5/601 |
| 6,122,538 A | * | 9/2000 | Sliwa et al. | 600/407 |
| 6,128,522 A | * | 10/2000 | Acker et al. | 600/411 |
| 6,374,132 B1 | * | 4/2002 | Acker et al. | 600/411 |
| 2002/0156365 A1 | * | 10/2002 | Tsekos | 600/411 |

FOREIGN PATENT DOCUMENTS

| DE | 199 05 239 A1 | 8/2000 | |
|---|---|---|---|
| EP | 0 627 206 A2 | 12/1994 | |
| JP | 9-24034 A | * 1/1997 | A61B/5/055 |
| WO | WO 98/52465 | 11/1998 | |

* cited by examiner

*Primary Examiner*—Hieu T. Vo
(74) *Attorney, Agent, or Firm*—Bingham McCutchen LLP

(57) ABSTRACT

An ultrasound therapy system utilizes a mechanical positioning assembly to locate and aim an ultrasonic transducer. The positioner provides for roll and pitch control as well as control in the lateral and longitudinal directions. The positioner uses piezo-electric vibrational motors that can effectively operate within the field of an MRI system without interfering with its operation. The motors are capable of providing a breaking force to the drive shafts while de-energized and thus aid in preventing motor slippage or backlash. Since the motors do not affect the operation of an MRI system, the ultrasonic therapy system can be made more compact. Two sets of position encoders are used to align the positioner. Course absolute encoders and fine relative encoders are both coupled to the positioning motors and allow for precise control over the position and orientation of the ultrasonic transducer.

19 Claims, 9 Drawing Sheets

MECHANICAL POSITIONER FOR MRI GUIDED ULTRASOUND THERAPY SYSTEM

FIELD OF THE INVENTION

The present invention pertains to a mechanical positioning system and more particularly, to a positioning system for an ultrasonic therapy device operating under Magnetic Resonance Imaging guidance.

BACKGROUND OF THE INVENTION

The use of Magnetic Resonance Imaging (MRI) is well-known. MRI provides a radiologist with detailed internal views of a patient's anatomy that cannot be visualized with conventional x-ray technology. Images generated by MRI systems provide physicians with a visual contrast between varying tissues that is extremely useful when planning surgical procedures.

Ultrasonic therapy uses focused, localized heating to selectively destroy tumors or other tissue anomalies. Heating tissue beyond a critical temperature for a period of time causes necrosis, the destruction of tissue. The use of MRI imaging to guide the focal point of an ultrasonic therapy device is known. For instance, U.S. Pat. Nos. 5,443,068, 5,275,165, and 5,247,935 each describe the use of an ultrasonic transducer, guided by an MRI system, to selectively destroy tissue. The details of these disclosures are hereby incorporated by reference into the present application.

The need to accurately position an ultrasonic transducer for use in selective tissue necrosis presents special problems when used in combination with an MRI guidance system. In particular, MRI systems employ large magnets, for creating a homogenous magnetic field, and gradient coils for altering that magnetic field in a uniform manner in time and/or space. This procedure creates magnetic field gradients. MRI systems also employ radiofrequency (RF) coils for applying an RF field to the tissue that is to be imaged, causing the tissue to resonate and create an MR response signal. The MR response signal is then used to construct an image of the tissue that is displayed to an operator. The image can then be printed or otherwise stored for later use and analysis. The degree of homogeneity of the magnetic field and the linearity of a magnetic field gradient over space and time are important in creating a clear undistorted image. Any interference with the RF field will reduce the quality of the image. The best and most consistent imaging typically occurs when surgical equipment or other objects do not interfere with the magnetic and RF fields created by the MRI system.

Several situations may affect the performance of MRI systems or other equipment used in conjunction with it. For example, equipment that is constructed from ferro-magnetic materials should not be used near an MRI system since the large magnetic fields generated by the MRI system will physically attract the magnetic equipment. Consequently, MRI performance may suffer. Furthermore, conductive materials disturb and distort the radio frequency electromagnetic fields necessary for resonance imaging. Other problems occur with materials that produce eddy currents when placed in a time-varying magnetic field. The eddy currents in these materials, usually electrical conductors, create their own magnetic field that interferes with the fields used for magnetic resonance imaging. Therefore, materials which exhibit good conductivity, such as aluminum and copper, should not be used within a time-varying magnetic field.

In order to accurately position an ultrasonic therapy device under MRI guidance, a precise positioning system must be employed. In addition, the positioning system needs to be able to provide repeatedly predictable control of the ultrasonic transducer in order to accommodate the precision requirements of certain clinical procedures. Tumors that may be small or have irregular shapes require exact positioning of the ultrasonic transducer in order to destroy only the intended tissue while leaving the healthy tissue undamaged.

Known positioning systems, such as those described in U.S. Pat. Nos. 5,247,935 and 5,275,165 utilize hydraulic mechanisms to position an ultrasonic transducer beneath a patient. However, these systems rely on placing the transducer directly beneath the object to be treated (e.g., a tumor) and provide positioning only in the linear x, y, and z axes. Due to constraints that may be imposed by the available acoustic passage to the object to be treated, effective therapy may not be possible with this arrangement. Additionally, these known systems have inherent reliability and accuracy problems due to the use of hydraulic positioners which can exacerbate motor backlash, degrading the accuracy of the positioner.

Since the motors used in these known systems are formed from materials that interfere with the operation of the MRI system, the motor must be placed at an increased distance from the ultrasonic transducer and the MRI imaging space. Known positioning systems therefore require the use of long motor drive shafts, which increase the physical footprint of the positioning system. Furthermore, the motors used in known systems need to be left engaged and energized in order to minimize slippage due to the backlash problem. Since an energized motor produces an increased electric field that interferes with the operation of a MRI system, the motor cannot be mounted within, or in the vicinity of, the MRI imaging space. For this reason, known systems require the motors to be mounted at a significant distance from the MRI imaging space.

U.S. Pat. No. 5,443,068 describes an MRI guided ultrasonic therapy system that uses threaded shafts attached to screw drives through universal joints in order to position the therapy transducer in three linear dimensions. The '068 patent also requires the ultrasonic transducer to be placed directly beneath the object to be treated and only provides positioning in the linear x, y, and z axes. The screw drives, and particularly the universal joints, utilized in this system compound the motor backlash problem described above and therefore further restrict the positional accuracy that the system can achieve. Furthermore, the motor drives of the '068 patent are formed from magnetic material and must also be located at a distance from the imaging space in order to eliminate interference with the MRI system.

SUMMARY OF THE INVENTION

The foregoing problems are solved by providing a positioning system for magnetic resonance imaging guidance of a therapy device. In a first embodiment, the position system comprises an energy transducer, a first positioner operative to adjust the location of the energy transducer in a lateral direction in a first plane, a second positioner operative to adjust the location of the energy transducer in a longitudinal direction in the first plane, and a third positioner operative to adjust the roll of the energy transducer.

Each of the positioners are vibrational motors that comprise a drive shaft and a linear actuator coupled to the drive shaft. The actuators are operative to produce a rotary motion of the drive shaft. The positioning system may further comprise a fourth positioner operative to adjust the pitch of the drive shaft.

In a further embodiment a device for positioning an ultrasonic therapy device under magnetic resonance imaging comprises a motor coupled to a drive shaft, a first position encoder coupled to the motor, and a second position encoder coupled to the drive shaft. The first position encoder is operative to measure the amount of motion relative to a predetermined position and the second position encoder is operative to measure the amount of motion relative to an arbitrary position.

In another embodiment, a device for positioning an ultrasonic therapy device under magnetic resonance imaging guidance comprises a vibrational motor coupled to a drive shaft, and a positioner assembly that includes a support bracket, a longitudinal slide coupled to the support bracket, and a lateral slide coupled to the longitudinal slide. The device may further comprise a second vibrational motor coupled to a second drive shaft, a third vibrational motor coupled to a third drive shaft, and a fourth vibrational motor coupled to a fourth drive shaft. Each of the vibrational motors controls a specific directional motion of the support bracket.

In a still further embodiment, a device for positioning an ultrasonic therapy device under magnetic resonance imaging guidance comprises energy concentrating means for directing energy at a focal point, a first positioning means for adjusting the lateral position of the energy concentrating means, a second positioning means for adjusting the longitudinal position of the energy concentrating means, and a third positioning means for adjusting the roll of the energy concentrating means. The device may further comprise a fourth positioning means for adjusting the pitch of the energy concentrating means.

Other and further aspects and advantages of the invention will become apparent hereinafter.

DETAILED DESCRIPTION OF THE PREFERRED EMBODIMENTS

Figure 1:
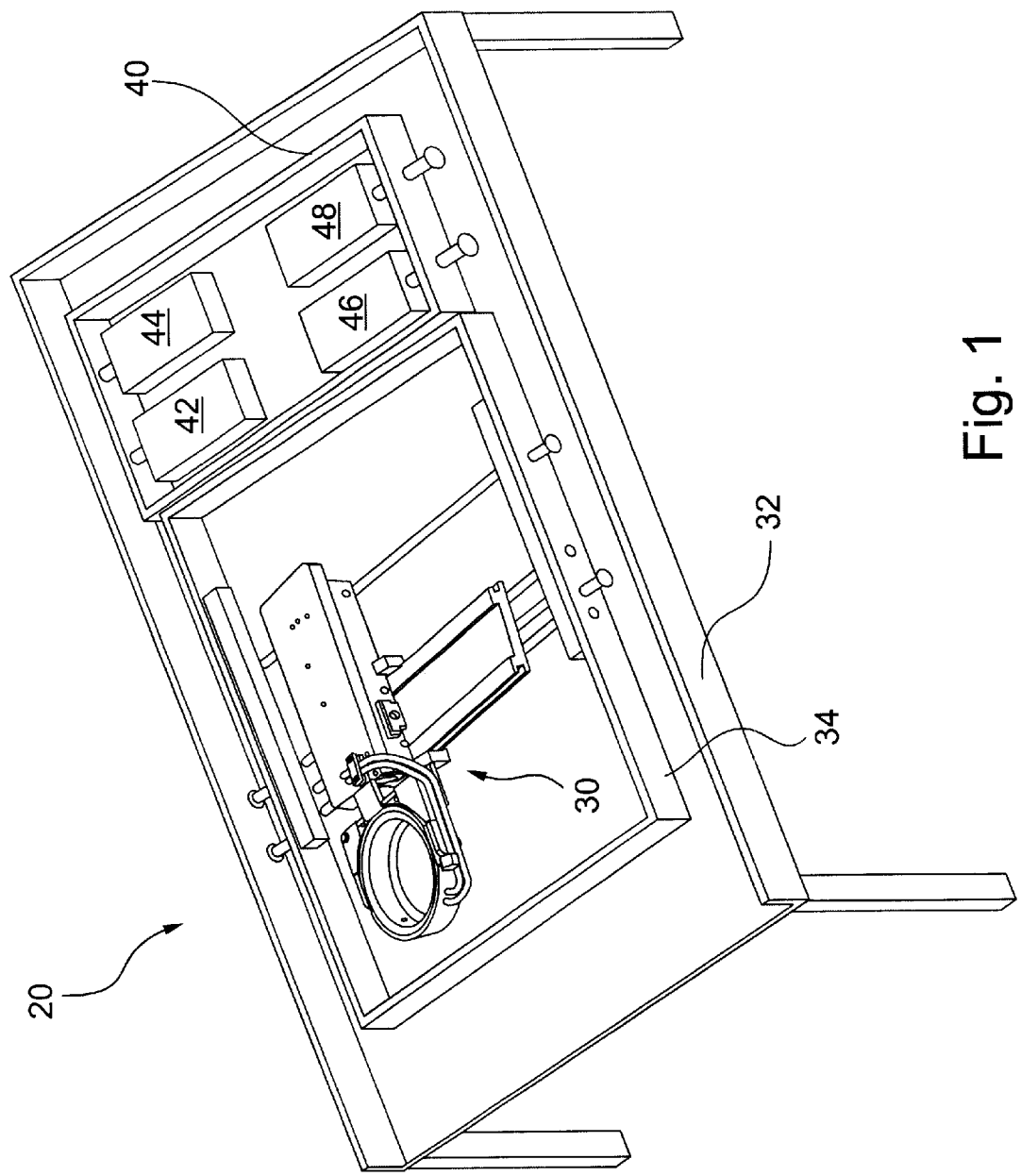
FIG. 1 is a perspective view of an ultrasound therapy system constructed in accordance with the present invention.
Figure 2:
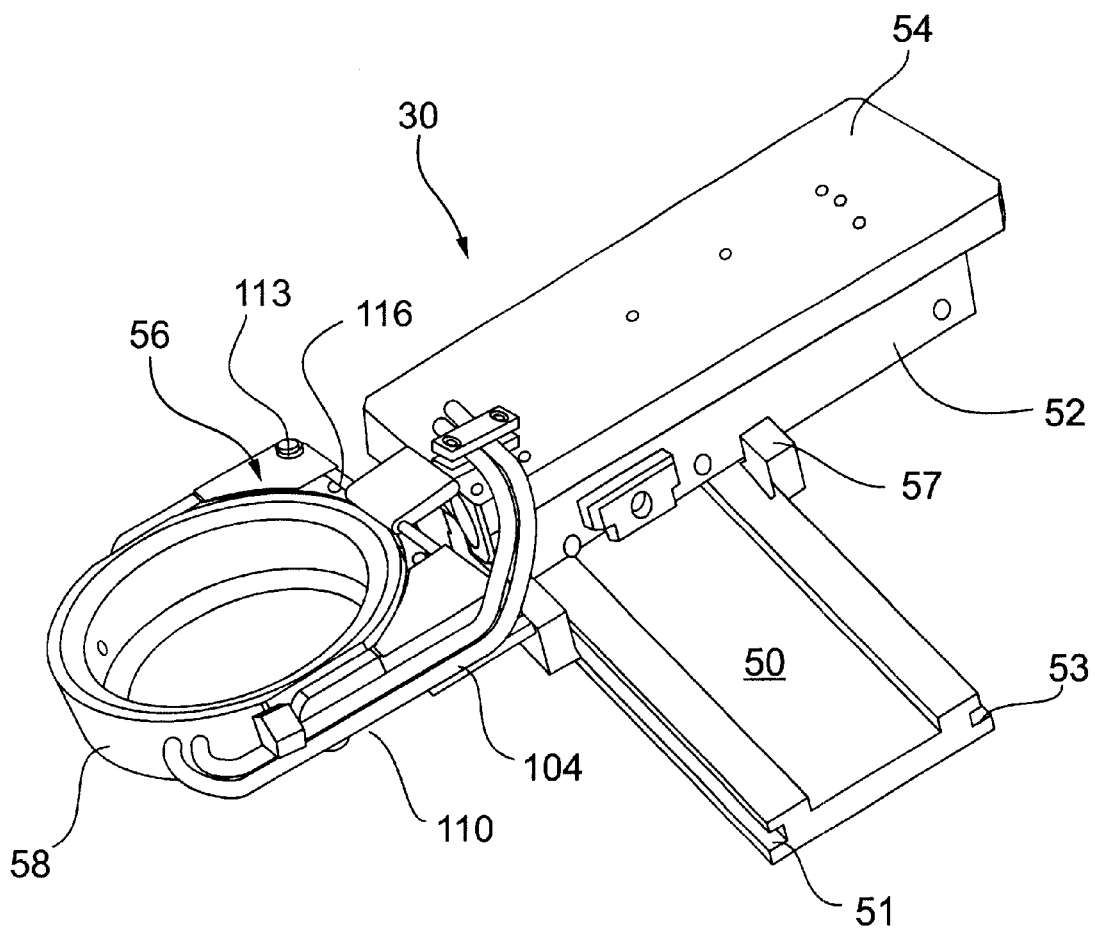
FIG. 2 is an isolated perspective view of a positioner used in conjunction with the ultrasound therapy system of FIG. 1.
Figure 3:
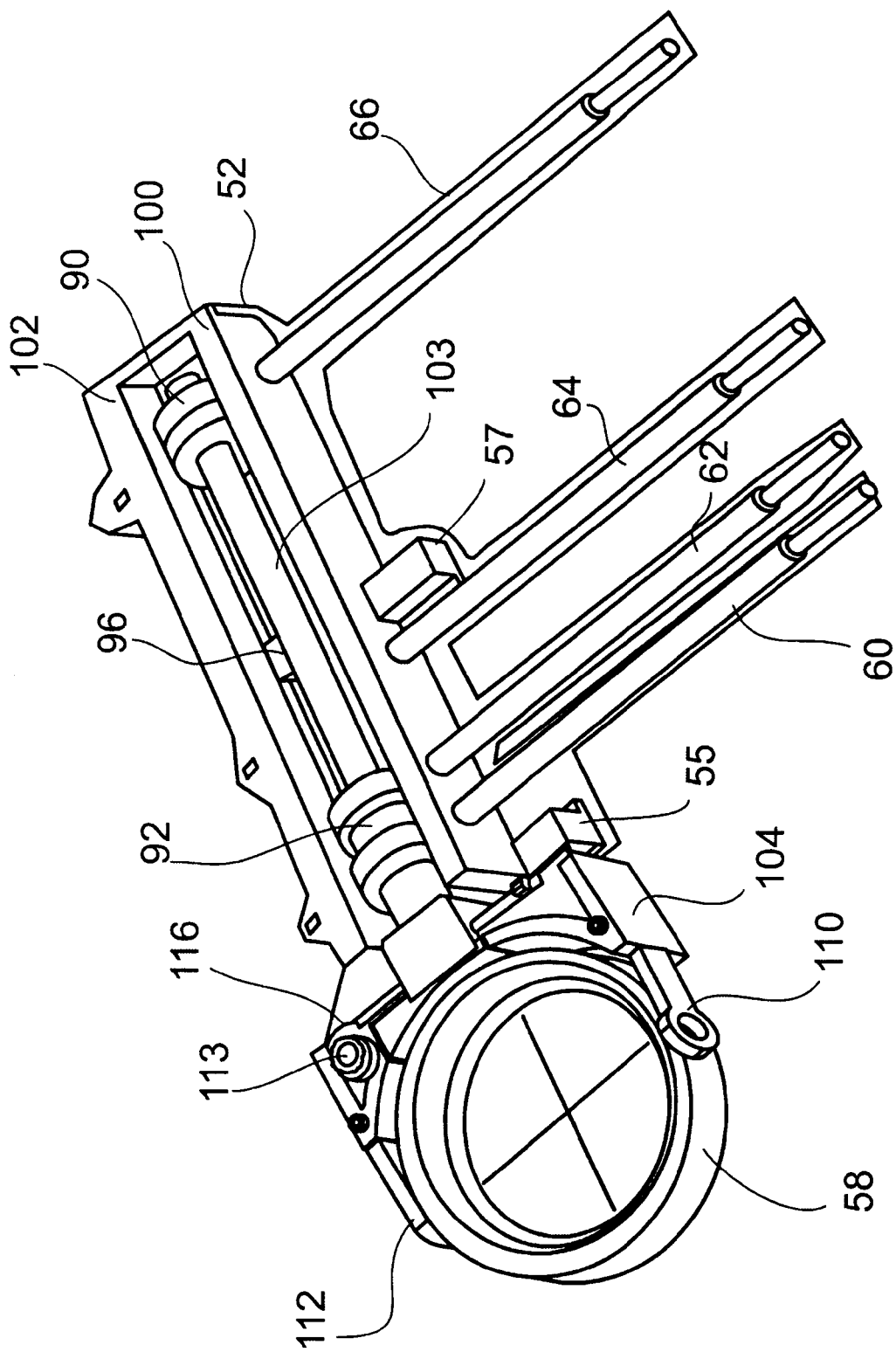
FIG. 3 is another isolated perspective view of a positioner used in conjunction with the ultrasound therapy system of FIG. 1.
Figure 4:
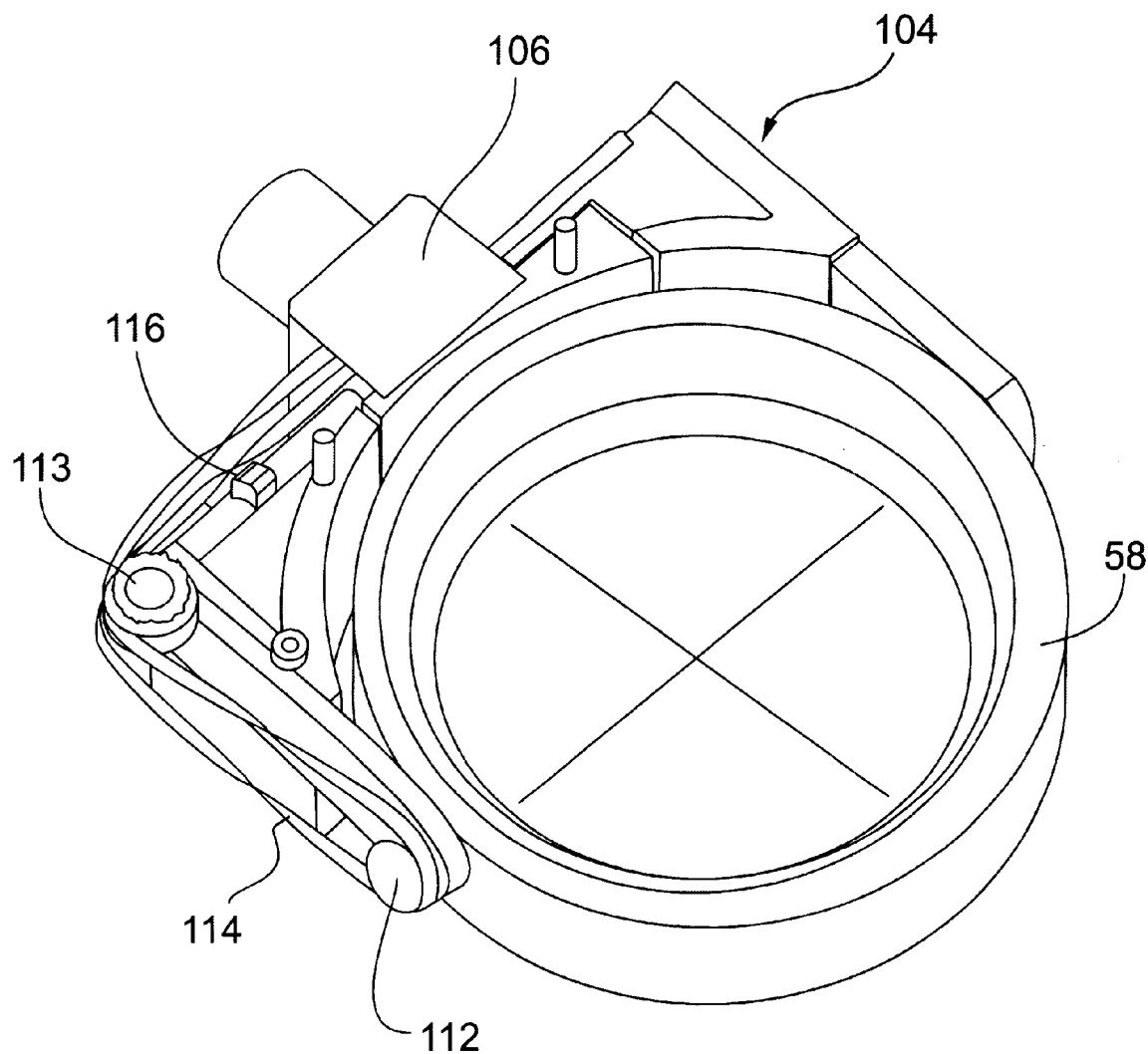
FIG. 4 is a perspective view of a transducer assembly and transducer holder used in conjunction with the positioner of FIGS. 2 and 3.
Figure 5:
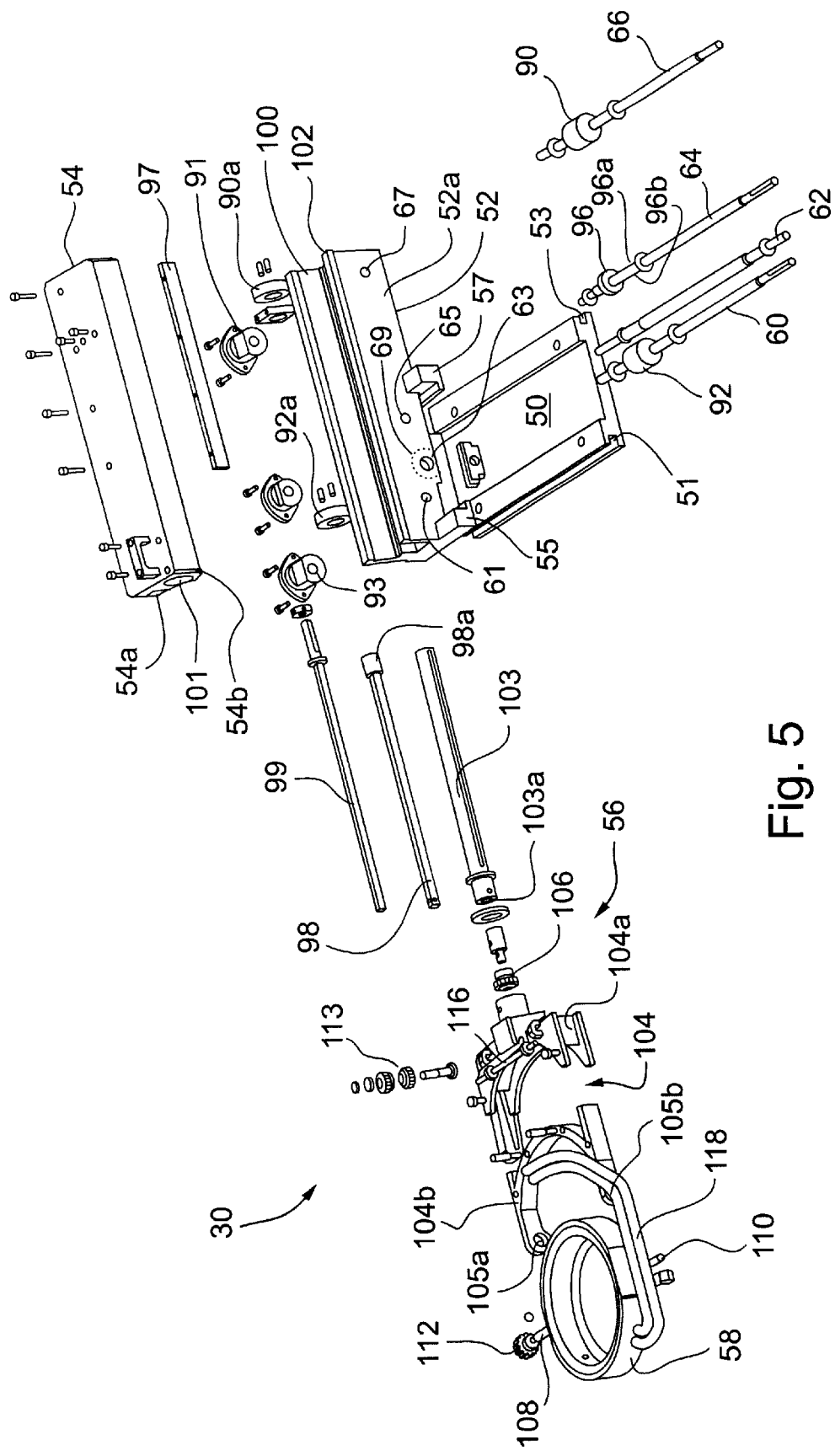
FIG. 5 is an exploded perspective view of a positioner used in conjunction with the ultrasound therapy system of FIG. 1.

FIG. 1 shows an ultrasound therapy system 20 constructed in accordance with the present invention. The ultrasound therapy system 20 is used in conjunction with an MRI based guidance system to accurately guide a physician to a desired therapy site. The ultrasound therapy system 20 includes an MRI cradle 32 that supports a positioner 30 and a motor bay 40. The positioner 30 is used to direct energy from an ultrasound or other energy transducer. The positioner 30 is mounted within a sealed case 34 and the motor bay 40 encloses four positioning motors 42, 44, 46, and 48. The motors 42, 44, 46, and 48 each provide rotary motion to a drive shaft and are each responsible for controlling a distinct motion direction of the positioner 30 (i.e., lateral, longitudinal, roll, or pitch). The vertical position of the ultrasonic energy is controlled electronically by altering the focal point of the ultrasonic transducer. Preferably, and as described in more detail below, the motors 42, 44, 46, and 48 are made from non-magnetic materials and impart a rotational motion on the respective drive shafts by utilizing piezo-electric vibrational fingers. The motor bay 40 is rigidly attached to the case 34 and forms a modular unit that is placed into and is attached to the MRI cradle 32. When assembled, the MRI cradle 32, including the case 34, the positioner 30, and the motor bay 40 are enclosed by a cover (best seen in FIG. 6). The ultrasound therapy system 20 is constructed so that a patient can be positioned on the cradle while the system is moved through an MRI imaging system. An ultrasonic transducer (not shown) is mounted on the positioner, and with guidance from the MRI system, a tumor or other tissue mass within a patient's body, can be precisely treated via ultrasonic energy. The ability to accurately position the ultrasonic transducer underneath a patient allows increased accuracy and efficiency of the ultrasonic therapy.

Referring to FIGS. 2 through 5, the positioner 30 is shown in further detail. Each component of the positioner 30 is made from an MRI-compliant material. In order to achieve a consistent and predictable ultrasonic energy application, the positioner 30, including the ultrasonic transducer, is submersed in a water bath during operation. Thus, the positioner components must also be made of a material that has good dimensional stability under water immersion conditions. The case 34 is filled with a degassed water to prevent cavitation of the positioner's moving parts and to ensure a consistent medium to transfer the ultrasonic energy from the transducer to the patient. All components of the positioner that penetrate the case 34 are appropriately sealed to prevent leakage.

The positioner 30 is composed of five main subassemblies: a base 50, a lateral slide 52, a longitudinal slide 54, a transducer holder 56, and a transducer assembly 58. Each of these subassemblies function together and are each mounted inside the case 34.

The base 50 is a generally flat plate that rigidly mounts the positioner 30 within the case 34. The base 50 has a front channel 51 and a back channel 53, both extending along the length of the base. The channels 51 and 53 provide a guide for, and enable precise, low-friction lateral movement (i.e., along the length of the base 50) of the remaining subassemblies of the positioner 30.

The lateral slide 52 is generally trough shaped and includes L-shaped rails 55 and 57 on its bottom surface that are perpendicular to its length. The rails 55 and 57 engage with the front channel 51 and the back channel 53, respectively, on the base 50. As such, the lateral slide 52 moves freely in the lateral direction only (i.e., along the length of the base 50). The motion of the lateral slide 52 is accomplished by a screw drive mechanism that includes a lateral positioning shaft 62 engaged with a corresponding nut 69 located inside the lateral slide 52. The lateral positioning shaft 62 is driven via the motor 46 located inside the motor bay 40 and engages with the lateral slide 52 through an aperture 63.

A roll positioning shaft 60 controls the roll motion of the positioner 30 and engages with the lateral slide 52 through an aperture 61. The roll positioning shaft 60 is driven via the motor 42. A longitudinal positioning shaft 64 controls the longitudinal motion of the positioner 30 and engages with the lateral slide 52 through an aperture 65. The longitudinal positioning shaft 64 is driven via the motor 44. A pitch positioning shaft 66 controls the pitch motion of the positioner 30 and engages with the lateral slide 52 through an aperture 67. The pitch positioning shaft 66 is driven via the motor 48. Each of the roll positioning shaft 60, the longitudinal positioning shaft 64, and the pitch positioning shaft 66 engage with the lateral slide 52 without impeding its ability to move laterally along the length of the base 50.

Figure 8:
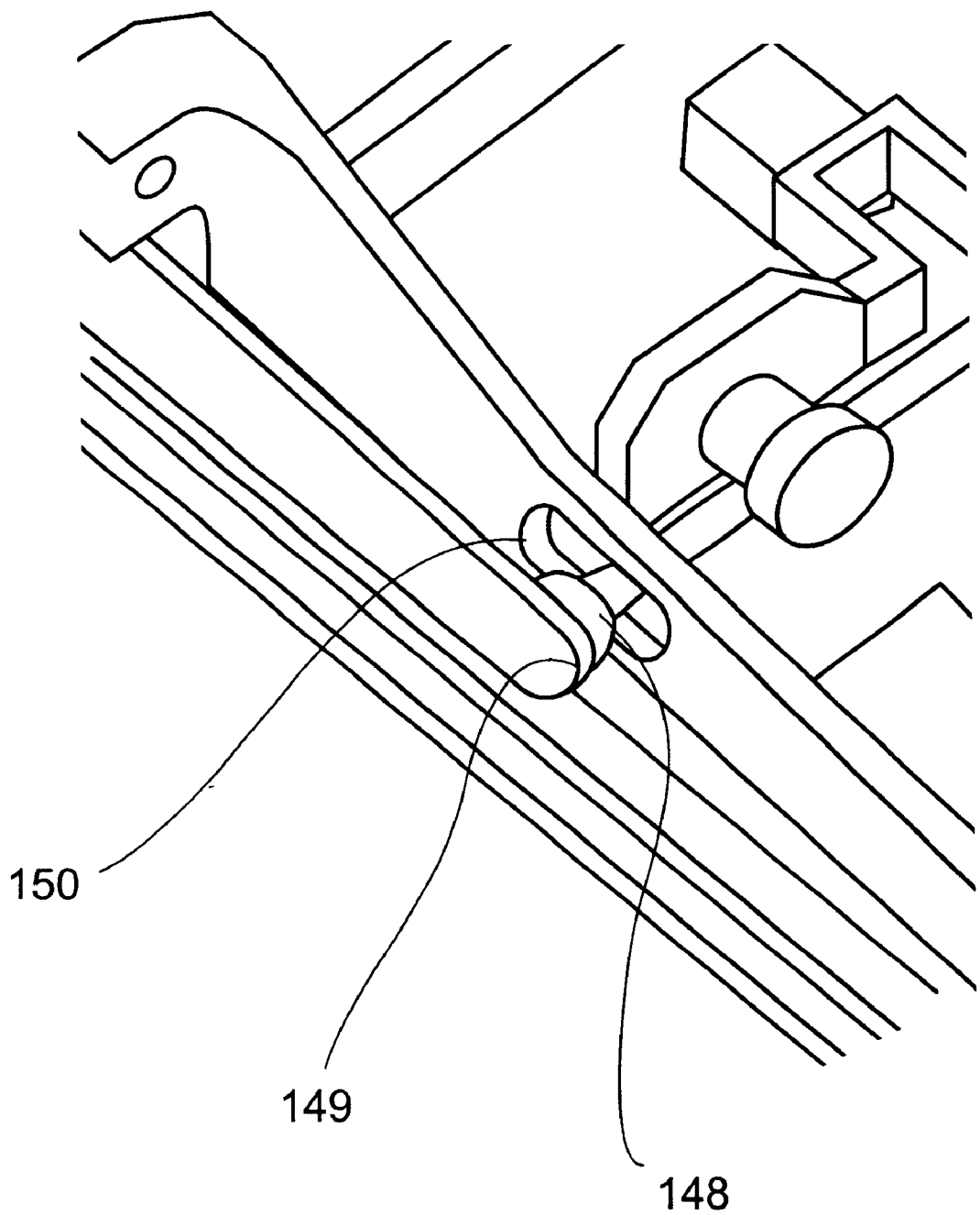
FIG. 8 is a detail showing the drive shaft of a positioning motor used in conjunction with ultrasound therapy system of FIG. 1.

Each of the motors 42, 44, 46, and 48 impart a rotary motion on the positioning shafts 60, 64, 62, and 66, respectively, through precision pulley and belt transmissions (best seen in FIG. 8). The rotary motion of the shafts is then translated into either a lateral, longitudinal, roll, or pitch movement of the positioner 30. The transmissions for translating the rotary motion of the shafts 60, 62, 64, and 66 into the corresponding movement of the positioner 30 are each within the lateral slide 52. It is noted that the arrangement of the motors within the motor bay 40, and their association with a specific positioning shaft, can vary.

The rotary motion of the longitudinal positioning shaft 64 is translated into a longitudinal motion of the positioner by a tooth gear 96 and a pair of sliding pins 96a and 96b. The rotary motion of the pitch positioning shaft 66 is translated into a pitch motion of the positioner by a first worm gear 90 and a spiral gear 90a, and the rotary motion of the roll positioning shaft 60 is translated into a roll motion of the positioner by a second worm gear 92 and a spiral gear 92a.

Housed within the lateral slide 53 are the driving transmissions for both the pitch and roll axes. The pitch transmission includes the spiral gear 90a that engages with the worm gear 90, and a round tube 98. The tube 98 has a shaped hole 98a that receives a shaft 99. The shaft 99 engages with the spiral gear 90a and is free to slide in and out of the tube 98 and induce the pitch motion by rotating. The roll transmission includes the spiral gear 92a that engages with the worm gear 92 and a shaft tube 103 that engages with the spiral gear 92a. A cap 91 closes the worm gear 90 within the lateral slide 52 and a cap 93 closes the worm gear 92 within the lateral slide 52. The upper portion of the lateral slide 52 includes rails 100 and 102 for engaging the longitudinal slide 54.

The longitudinal slide 54 includes channels 54a and 54b that engage with the rails 100 and 102 on the lateral slide 52. This enables the longitudinal slide 54 to move along the length of the lateral slide 52. The longitudinal motion of the longitudinal slide 54 and the positioner 30 is accomplished by engaging the tooth gear 96 with a tooth bar 97 that is mounted to the bottom surface of the longitudinal slide 54. The matching level of the tooth bar 97 to the tooth gear 96 is adjustable so that backlash in the movement of the longitudinal slide is minimized.

The transducer holder 56 engages with the shaft tube 103 and includes a holding fork 104. The holding fork 104 is formed from two separate pieces, a sprocket assembly 104a and a support bracket 104b. The shaft tube 103 engages on its proximal end with an opening 101 in the longitudinal slide 54, and engages on its distal end with the sprocket assembly 104a of the holding fork 104. The distal end of the shaft tube 103 is the end closer to the transducer assembly. Any longitudinal motion of the longitudinal slide 54 is therefore directly translated to the shaft tube 103 and the holding fork 104. Similarly, since the holding fork 104 is directly attached to the shaft tube 103, any roll motion of the shaft is directly applied to the fork.

The shaft tube 103 contains a lumen 103a formed to receive the tube 98. The distal end of the tube 98 engages the sprocket assembly 104a through the inner passage 103a and when so engaged, has a longitudinal axis common to the longitudinal axis of the shaft tube 103. With this arrangement, the pitch driving mechanism described above, and engaged with the tube 98, can provide a pitch motion to the positioner 30, regardless of the orientation of either the longitudinal slide 54 or the transducer holder 56. A sprocket wheel 106 is mounted on the distal end of the tube 98 and transfers the rotational motion of the shaped hole 98a to the sprocket assembly 104a.

The transducer assembly 58 is mounted to the transducer holder 56 by two shafts, 108 and 110, that fit through holes 105a and 105b in the support portion 104b of the fork 104. The transducer assembly 58 is preferably a cup-shaped component that is adapted to receive a correspondingly shaped ultrasonic transducer element (not shown). The transducer assembly 58 is also sized to engage with the holding fork 104 and to rotate freely about the shafts 108 and 110. A sprocket wheel 112 is mounted on the end of the shaft 108 and another sprocket wheel 113 is mounted on the corresponding side of the sprocket assembly 104a. The sprocket wheel 113 is formed from two counter-rotating sprockets mounted one on top of each other on a common drive shaft. A chain 114 connects the sprocket wheels 112, 113, and 106, and translates the rotational motion of the tube 98 into a pitch motion of the transducer assembly 58. A tensioning mechanism 116 ensures that the chain 114 remains taught and transfers the rotary motion of the tube 98 with minimal backlash. Cables 118 provide power to the transducer element and relay data back to an operator.

Figure 6:
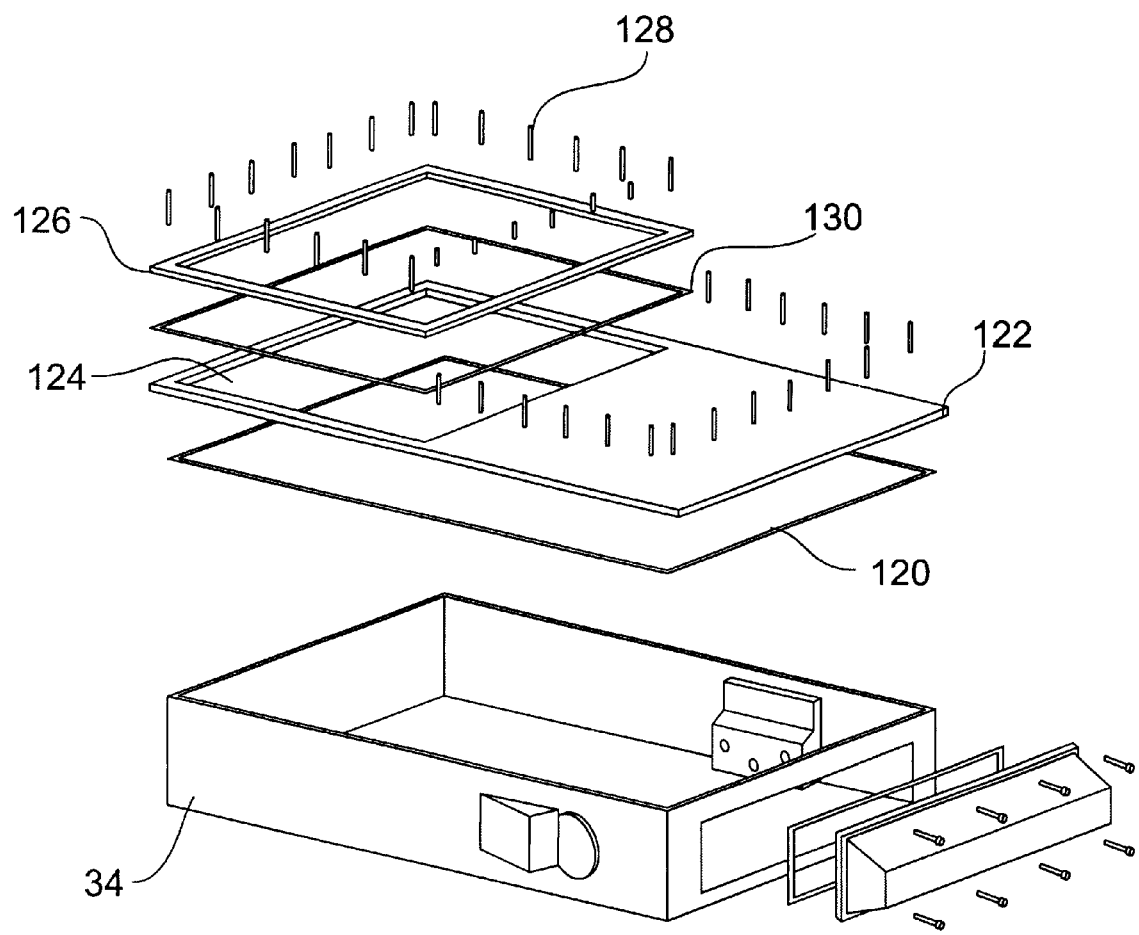
FIG. 6 is a perspective view of a case that encloses the positioner.

Referring to FIG. 6, the case 34 that encloses the positioner 30 is shown in greater detail. Since the case is filled with degassed water during operation of the transducer, it is necessary to seal all openings and mounting interfaces. This is preferably accomplished with an O-ring or another type of flexible seal. The case 34 includes a cover 122 that is bolted to the top perimeter of the case and sealed with an O-ring 120. A mylar panel 124 is embedded in the cover and is positioned over the location of the transducer element. The mylar panel 124 is attached to the cover 122 with a frame 126 and is sealed with an O-ring 130. The mylar panel 124 ensures a consistent interface to the MRI imaging area and protects the imaging area from damage.

Figure 7:
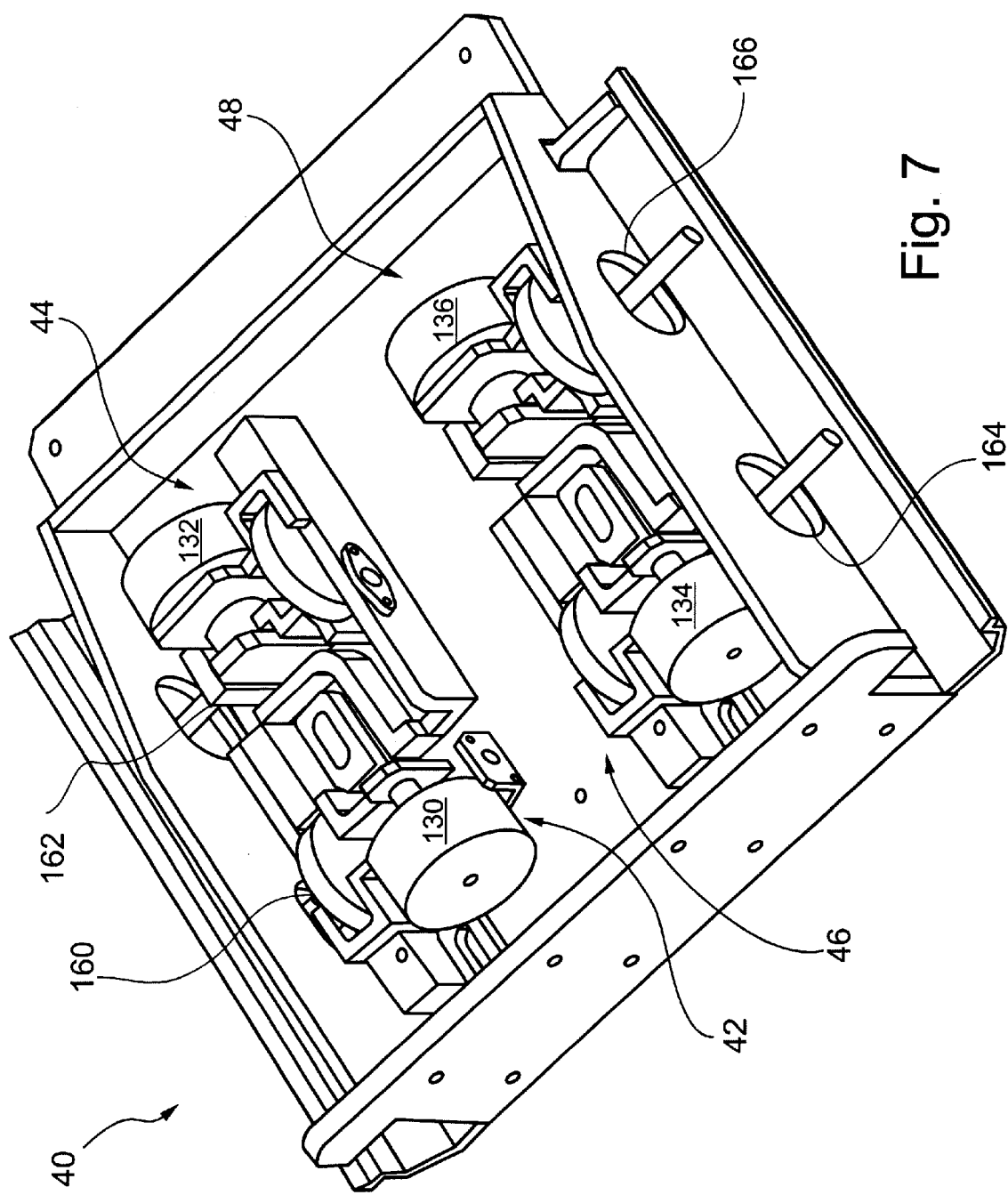
FIG. 7 is a perspective view of a motor bay used in conjunction with the ultrasound therapy system of FIG. 1.
Figure 9:
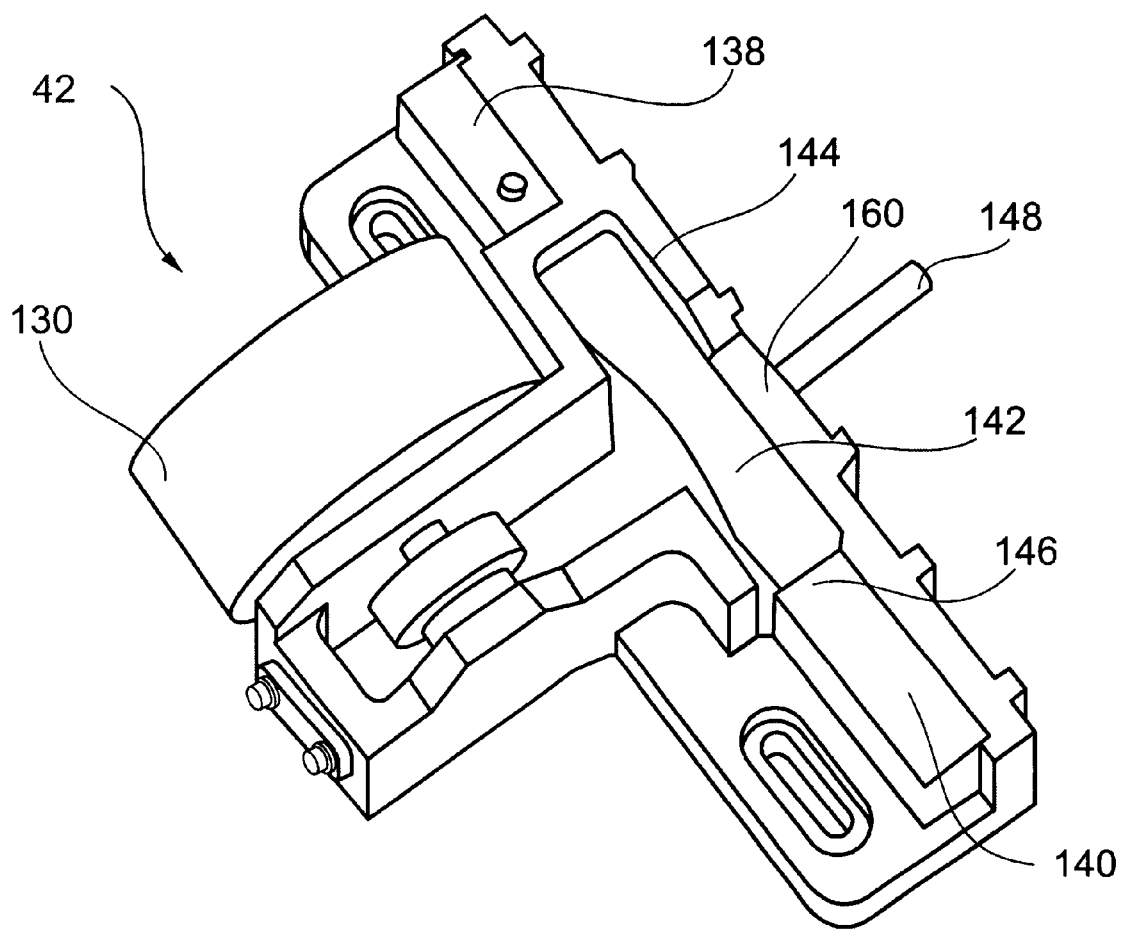
FIG. 9 is a detail of a motor used in conjunction with the ultrasound therapy system of FIG. 1.

Turning to FIGS. 7 through 9, the motor bay 40 is shown in more detail. FIG. 7 depicts the four motors 42, 44, 46, and 48 mounted inside the motor bay 40. Each of the motors produce a rotary motion that is ultimately transferred to the four positioning shafts 60, 64, 62, and 66, respectively, via precision pulley and belt transmissions. Each one of the motors is responsible for a distinct motion direction of the positioner (i.e., lateral, longitudinal, roll, and pitch). FIG. 8 shows a typical detail of a motor drive shaft 148 attached to a precision pulley 149 which in turn engages with a belt 150. The belt 150 extends along the length of the case 34 and is then attached to one of the positioning shafts extending from the case 34. A similar pulley is attached to each of the positioning shafts. The rotary motion produced by each of the motors is thus transferred to the positioning shafts, which in turn translate the rotary motion into one of the distinct motion directions of the positioner 30.

Specifically, the motor 42 is coupled to the roll position shaft 60 and is responsible for the roll direction of the positioner 30. The motor 44 is coupled to the longitudinal position shaft 64 and is responsible for the longitudinal direction of the positioner 30. The motor 46 is coupled to the lateral position shaft 62 and is responsible for the lateral direction of the positioner 30. And the motor 48 is coupled to the pitch position shaft 66 and is responsible for the pitch direction of the positioner 30.

Precise control of each positioner motion direction is necessary when aiming an ultrasound or other energy transducer. Particularly when providing therapy to small tissue masses or an area of a patient that is obscured by varying tissue properties. In order to achieve and maintain this precise control, an ultrasonic therapy system constructed in accordance with the present invention utilizes two sets of position encoders.

The angular position of each motor is measured by an absolute encoder 130, 132, 134, or 136. One example of such an encoder is model No. A2-S-K-250, manufactured by U.S. Digital Corporation. Each of the motors 42, 44, 46, and 48 are based on a pair of linear actuators such as those manufactured by Nanomotion Ltd. Each of the actuators have two piezo-electric vibrational fingers. The actuators are designed to drive the vibrational fingers in a linear direction.

Referring to FIG. 9, the motor 42 is shown in greater detail. The motor 42 has two actuators 138 and 140, fixed on either side of a ring 142. The ring is preferably made from alumina or another hard, non-magnetic material. The actuators 138 and 140 are positioned 180° apart around the circumference of the ring 142. A pair of vibrational fingers 144 are attached to the actuator 138 and a pair of vibrational fingers 146 are attached to the actuator 140. Each pair of vibrational fingers 144 and 146 include tension springs (not shown) that fasten them to the ring 142. The tension springs produce a high amount of friction between the fingers and the ring and results in the fingers acting as a break for the ring when the fingers are still (i.e., not energized by the actuators). When the fingers vibrate (i.e., energized by the actuators), the linear motion of the fingers translates into a rotary motion of the ring. The rotation of the ring 142 drives the motor shaft 148, which in turn drives both the transmission (the pulley and belt system described above), and the absolute encoder 130. All components of the motor assembly are made of non-magnetic materials such as plastic, brass, alumina, etc. so that they can be used within the magnetic field of a MRI system without interfering with its performance.

An ultrasonic therapy system constructed in accordance with the present invention further utilizes a second set of encoders, more specifically "relative encoders." The first set, referred to as "absolute encoders", and mentioned briefly above, are mounted directly on each of the motor assemblies and measure the absolute amount of motion relative to the origin location of the positioner. The origin is designated as the "home" position.

The second set of encoders 160, 162, 164, and 166, ("relative encoders"), are mounted on each of the drive shafts of the motors and measure the amount of motion relative to the position of the system at the time of system power-up. One such example of a relative encoder is model No. HD-9140 manufactured by Hewlett Packard. As can be expected, the position of the system at power-up need not be, and in most cases, is not, the same as the "home" position. Rather, this position is an arbitrary position that was reached during the previous operation and prior to powerdown. The absolute encoders provide a course positioning measurement and the relative encoders provide a fine positioning measurement. Both the relative and the absolute encoders are preferably shielded by a copper cup in order to prevent RFI disturbances induced by the MRI system.

The relative encoders provide enough motion resolution to support the accuracy requirements of an ultrasound therapy system. They also have a very compact footprint in order to comply with the slim dimension of the case 34. It is also preferable to select encoders that support an indexing feature. The index is a point on the encoder that is encountered once per revolution. It should be noted that the encoder typically performs more than one revolution within the positioner's complete range of motion.

In order to bring the system to the home position after power-up and to properly initialize the relative encoders, the positioner is brought to the vicinity of the home position based on the measurements of the absolute encoders. Since these readings are not accurate to the extent that the system demands, the home location is fine tuned by utilizing the higher resolution of the relative encoders. The relative encoders typically have up to 10 times the resolution of the absolute encoders. During an initial calibration procedure, the value of each encoder's index position around the home position is pre-stored. Once the positioner is in the vicinity of the home position, the positioner is moved until the index position of the associated relative encoder is reached. At that point, the current value of the encoder is reset to the calibrated pre-stored value and the positioner is moved back to the home position based on the relative encoder position readings.

Dual positioner readings are further utilized to detect any single failure in the absolute or relative encoders or in the actuator controller by comparing the respective values of the absolute and relative encoder readings. Any discrepancy triggers a safety mechanism that either performs some automatic recovery routine or stops any further motion until human intervention occurs.

Each of the motors described above act as a breaking system allowing all power to the positioner to be disconnected while MR imaging is taking place. The breaking feature of the motors holds the transducer position without the risk of positional slip and without the potential for backlash. Known motors used in MR imaging systems require power to be continuously supplied in order to provide a breaking force and therefore require that the motors be located remote from the MRI system so that they do not interfere with the MRI performance. With a positioning system constructed in accordance with the present invention, and since the motors can be de-energized while the MR imaging system is activated, the motors can be located closer to the imaging volume and the entire system can be made more compact.

An ultrasonic therapy system constructed in accordance with the present invention thus allows the positioning motors to operate within the MRI imaging space without interfering with the operation of the MRI system. Since inadvertent motor motion at a treatment location due to backlash can be prevented without the need to energize and engage the motors, and since the motors are made from non-magnetic components, the motor bay can be located close to the positioner and within the MRI imaging space.

Although the invention has been described and illustrated in the above description and drawings, it is understood that this description is by example only and that numerous changes and modifications can be made by those skilled in the art without departing from the true spirit and scope of the invention. The invention, therefore, is not to be restricted, except by the following claims and their equivalents.

What is claimed is:

1. Apparatus for positioning a therapy device operated under magnetic resonance imaging guidance, comprising:
   a first vibrational motor operative to adjust a location of the therapy device in a lateral direction in a first plane;
   a second vibrational motor operative to adjust a location of the therapy device in a longitudinal direction in the first plane; and
   a third vibrational motor operative to adjust a roll of the therapy device.

2. The positioning apparatus of claim 1, further comprising a positioner operative to adjust a pitch of the therapy device.

3. The positioning apparatus of claim 1, further comprising an encoder coupled to each of the first, second, and third vibrational motors.

4. The positioning apparatus of claim 3, wherein the encoder is an absolute encoder.

5. The positioning apparatus of claim 3, wherein the encoder is a relative encoder.

6. The positioning apparatus of claim 1, each vibrational motor comprising
   a drive shaft; and
   a linear actuator coupled to the drive shaft and operative to rotate the drive shaft.

7. The positioning apparatus of claim 1, each vibrational motor comprising
   a drive shaft; and
   a piezo-electric element coupled to the drive shaft and operative to rotate the drive shaft.

8. The positioning apparatus of claim 7, wherein the respective piezo-electric element in each vibrational motor comprises mechanical fingers serving to rotate the respective drive shaft when the piezo-electric element is energized, the mechanical fingers further serving as a respective drive shaft brake when the piezo-electric element is not energized.

9. The positioning apparatus of claim 1, each vibrational motor comprising
   a drive shaft;
   a ring engaged with the drive shaft, the ring formed from a non-magnetic material; and
   a piezo-electric element coupled to the ring and operative to rotate the ring.

10. The positioning apparatus of claim 9, wherein the respective piezo-electric elements include tension springs operative to engage the respective rings.

11. The positioning apparatus of claim 9, further comprising an absolute encoder coupled to the drive shaft of each vibrational motor.

12. The positioning apparatus of claim 1, wherein the vibrational motors are formed from non-magnetic materials, such that the positioning apparatus can be operated in a MRI system imaging space without interfering with performance of the MRI system.

13. The positioning apparatus of claim 12, wherein the non-magnetic material is one or more of plastic, brass, or alumina.

14. The positioning apparatus of claim 1, wherein the therapy device is an ultrasound transducer.

15. Apparatus for positioning a therapy device under magnetic resonance imaging guidance, comprising:
    a motor coupled to a drive shaft;
    a first position encoder coupled to the motor; and
    a second position encoder coupled to the drive shaft.

16. The apparatus of claim 15, wherein the motor is a vibrational motor.

17. The apparatus of claim 15, wherein the first position encoder is operative to measure an amount of motion relative to a predetermined position, and wherein the second position encoder is operative to measure an amount of motion relative to an arbitrary position.

18. The apparatus of claim 15, wherein the first position encoder is an absolute encoder, and wherein the second position encoder is a relative encoder.

19. The positioning apparatus of claim 15, wherein the therapy device is an ultrasound transducer.

* * * * *